United States Patent [19]
Lee et al.

[11] Patent Number: 5,672,775
[45] Date of Patent: Sep. 30, 1997

[54] METHOD OF SEPARATING PHENOL FROM HIGHLY CONCENTRATED PHENOL SOLUTION

[75] Inventors: Huen Lee; Ji-Ho Yoon, both of Taejon, Rep. of Korea

[73] Assignee: Korea Advanced Institute of Science and Technology, Taejon, Rep. of Korea

[21] Appl. No.: 591,964

[22] Filed: Jan. 29, 1996

[30] Foreign Application Priority Data

Feb. 14, 1995 [KR] Rep. of Korea .................. 95-2670

[51] Int. Cl.$^6$ ........................................... C07C 37/70
[52] U.S. Cl. ................................. 568/749; 568/754
[58] Field of Search .................................. 568/749

[56] References Cited

FOREIGN PATENT DOCUMENTS 1538212  1/1979  United Kingdom .

OTHER PUBLICATIONS

Ghonasgi, D. et al. *Measurement and Modeling of Supercritical Carbon Dioxide Extration of Phenol from Water*, The Journal of Supercritical Fluids, 4:53–59 (1991).

Gupta, S. et al. *Supercritical Carbon Dioxide Extraction . . .*, The Journal of Supercritical Fluids, 4:181–185 (1991).

Roop, Robert K. and Akgerman, Aydin *Entrainer Effect for Supercritical Extraction of Phenol from Water*, Ind.Eng.Chem.Res., 28(10):1542–1546 (1989).

Ghonasgi, D. et al. *Supercritical $CO_2$ Extraction of Organic Contaminants from Aqueous Streams*, AIChE Journal, 37(6):944–950 (1991).

Roop et al. *Supercritical Extraction of Pollutants from Water and Soil*, ACS Symposium Series of Supercritical Fluid Science and Technology, 468–476 (1989).

*Primary Examiner*—Alan L. Rotman
*Assistant Examiner*—Sreeni Padmanabhan
*Attorney, Agent, or Firm*—Darby & Darby

[57] ABSTRACT

The present invention relates to a method of separating and purifying phenol in a simple and economical manner, by employing a step of adding high pressure carbon dioxide to the aqueous phenol solution to form a solid clathrate of phenol. According to the method of separating phenol of the present invention, phenol can be separated from the highly concentrated phenol solution without employing solvent or post-treatment step, finally to give 100 mole % of a solid phenol and 0.6 mole % of an aqueous phenol solution by employing only one step. Moreover, since the method is carried out at the temperature of below room temperature without excess energy consumption, the separation of phenol can be made in a simple and economical manner.

5 Claims, 3 Drawing Sheets

METHOD OF SEPARATING PHENOL FROM HIGHLY CONCENTRATED PHENOL SOLUTION

FIELD OF THE INVENTION

The present invention relates to a method of separating phenol from a highly concentrated phenol solution, more specifically, to a method of separating and purifying phenol in a simple and economical manner, by employing a step of adding high pressure carbon dioxide to the aqueous phenol solution to form a solid clathrate of phenol.

BACKGROUND OF THE INVENTION

Phenol cannot be easily separated from an aqueous phenol solution, which is grounded that phenol exists in an aqueous solution as liquid—liquid two phases, depending on the concentration ratio thereof. In particular, it is very difficult to separate phenol from a highly concentrated phenol solution containing phenol of about 30 mole % or more.

Conventional methods of separating phenol from such a highly concentrated phenol solution employing distillation or membrane have been used in the art. Both of the methods, however, suffer from the drawbacks that they essentially accompany post-treatment step and perfect separation of phenol is impossible; and, therefore, they have revealed a serious limitation in practical application.

For example, GB Patent No. 1,538,212 discloses a method of recovering phenol from an aqueous effluent produced from a phenol/aldehyde resin plant, which comprises the steps of extracting the effluent with solvent and separating the phenol from the resultant extractant by distillation. However, since the prior art process essentially accompanies a distillation procedure which requires extra high energy, it has not been practically applied in the art. Moreover, the method suffers from the following drawbacks: it essentially requires a subsequent step to remove the used solvent; and, it does not give pure phenol of purity 100%.

Accordingly, there exists a need in the art for the development of a more simple and economical method of separating phenol from a highly concentrated phenol solution.

Meanwhile, it has been known that some organic compounds and low-molecular gases undergo a physical reaction to give a crystalline molecule which is called as "clathrate"; and, water and several quinol compounds have been reported to form the clathrate. The clathrate is made up of a host which constitutes a skeleton and a guest which is essentially required for stabilizing the host under the unstable state: for example, water and quinol compounds are fallen within the host, while low-molecular gases such as argon, krypton, nitrogen, oxygen, methane, xenon, hydrogen sulphide and carbon dioxide are classified as the guest. A clathrate whose host is water, specifically, has been called as "gas hydrate", and has been actively studied in the art. However, as for the clathrates of quinol compounds including phenol, only structural characteristics thereof have been hitherto studied; and, thermodynamic properties and their application have not been elucidated in a detailed manner.

Under the circumstances, the present inventors have made a series of studies on the clathrate of phenol with a view to separate phenol from a highly concentrated phenol solution, and developed a method of separating phenol of 100 mole %, by employing a step of adding high pressure carbon dioxide to the aqueous phenol solution, to form a solid clathrate in which the host is phenol present in the aqueous solution and the guest is inexpensive and non-toxic carbon dioxide.

SUMMARY OF THE INVENTION

In accordance with the present invention, it has been discovered that phenol can be separated from a highly concentrated phenol solution, by employing a method which comprises a step of adding high pressure carbon dioxide to the aqueous phenol solution to form a solid clathrate.

A primary object of the present invention is, therefore, to provide a method of separating phenol from a highly concentrated phenol solution in a simple and economical manner.

BRIEF DESCRIPTION OF THE DRAWINGS

The above and the other objects and features of the present invention will become apparent from the following descriptions given in conjunction with the accompanying drawings, in which.

DETAILED DESCRIPTION OF THE INVENTION

A method of separating phenol from a highly concentrated phenol solution of the present invention, comprises a step of adding high pressure carbon dioxide to the aqueous phenol solution to form a solid clathrate. According to the method, the pressure of carbon dioxide is controlled in the range of 15 to 100 bar, preferably 15 to 45 bar; and, the clathrate is formed at the temperature of 0° to 43° C., preferably 0° to 20° C.

The method of separating phenol from an aqueous phenol solution is chiefly carried out at the temperature of below room temperature, while conventional separation methods of prior art require high temperature. Accordingly, the separation of phenol can be made without excess energy consumption, finally to give 100 mole % of a solid phenol and 0.6 mole % of an aqueous phenol solution, by employing only one step.

The method of separating phenol of the present invention can also be applied to the separation of quinol compounds from highly concentrated solutions containing the materials by employing the quinol compounds, instead of phenol, as a host, and hydrogen sulphide, nitrogen, methane and air, instead of carbon dioxide, as a guest, respectively. Further, the method can effectively separate phenol from the mixtures containing organic compounds in addition to phenol.

The present invention is further illustrated by the following examples, which should not be taken to limit the scope of the invention.

EXAMPLE 1

Figure 1:
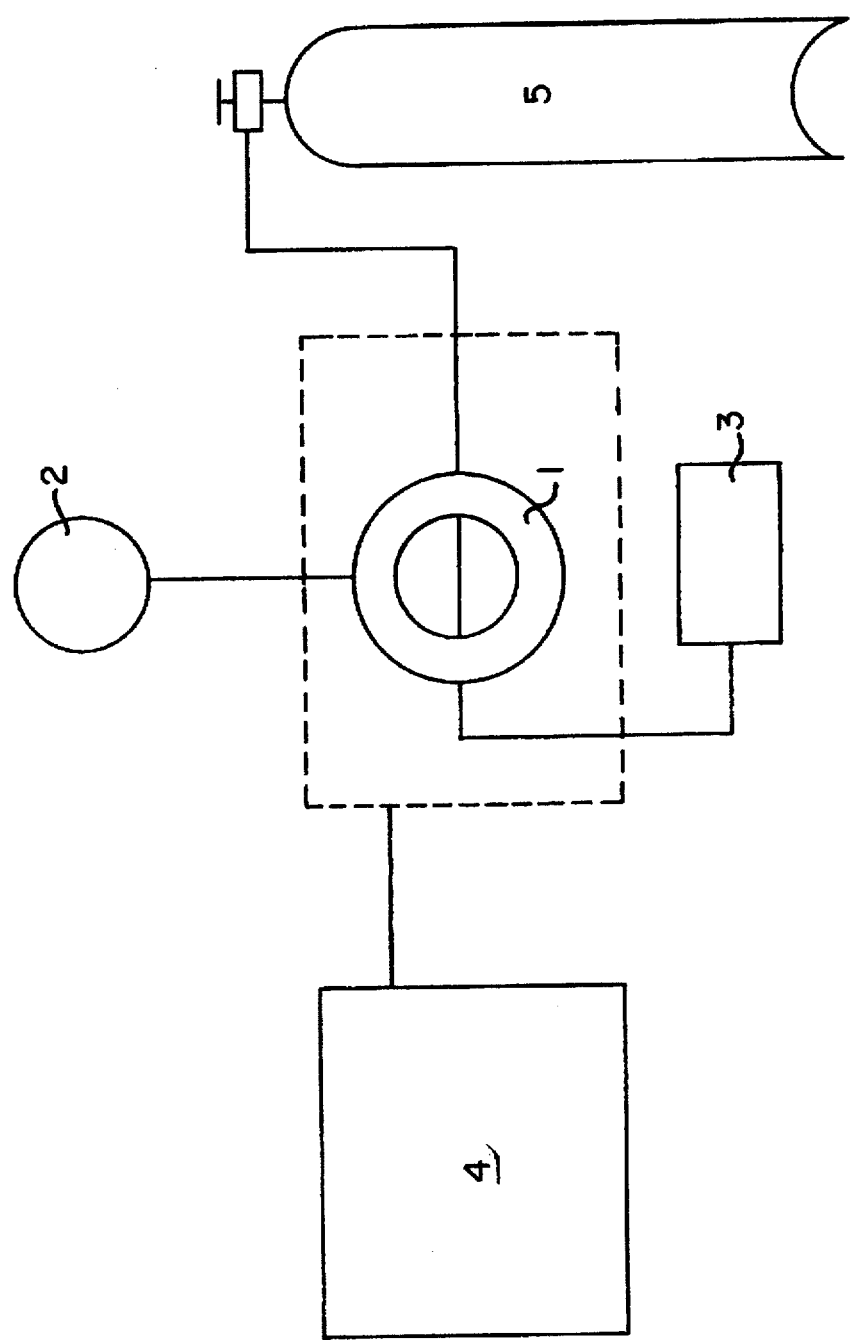
FIG. 1 is a schematic diagram depicting a high pressure phase equilibrium apparatus employed in the present invention.

A high pressure phase equilibrium apparatus depicted in FIG. 1 was employed, to determine the ranges of temperature and pressure at which the interested phenol clathrate is formed, and to measure phase equilibrium data. As shown in FIG. 1, the phase equilibrium apparatus comprises: a high pressure equilibrium cell(1) for monitoring the high pressure phase equilibrium; a manometer(2) for measuring the pressure; a thermometer(3) for measuring the temperature; a gas chromatograph(4) for analyzing components of the respective phases formed; a carbon dioxide reservoir(5); and, optionally a pressurization part and high pressure valves for the influx of high pressure carbon dioxide.

The present inventors first removed impurities from the phase equilibrium apparatus with the aid of a vacuum pump, put an aqueous phenol solution into an equilibrium cell(1), and maintained at a constant temperature lower than that of experimentation by about 5° C. Then, carbon dioxide was pressurized to reach a constant pressure using high pressure valves of the pressurization part, and a magnetic spin bar placed in the interior of the cell(1) was rotated to initiate a clathrate-forming reaction. After stirring for about 1 to 4 hrs, the formation of a solid phenol clathrate was observed by the naked eye. When the reaction was carried out to some extent, the level of the clathrate was checked, while slowly elevating the temperature to a predicted value. When the level of the phenol clathrate was maintained constantly for about 8 hrs, an equilibrium value was taken, and components which exist in the respective phases were analyzed using the gas chromatograph(4).

Three-phase, i.e., vapour-liquid water-hydrate, equilibria for the binary water-carbon dioxide system were measured using the phase equilibrium apparatus. As can be seen in the results( - - □ - - ) of FIG. 2, the dissociation pressures at the temperature of 2.2°, 4.6°, 6.9°, 9.2° and 10.1° C. were determined as 15.6, 21.0, 28.2 and 45.2 bar, respectively.

Figure 2:
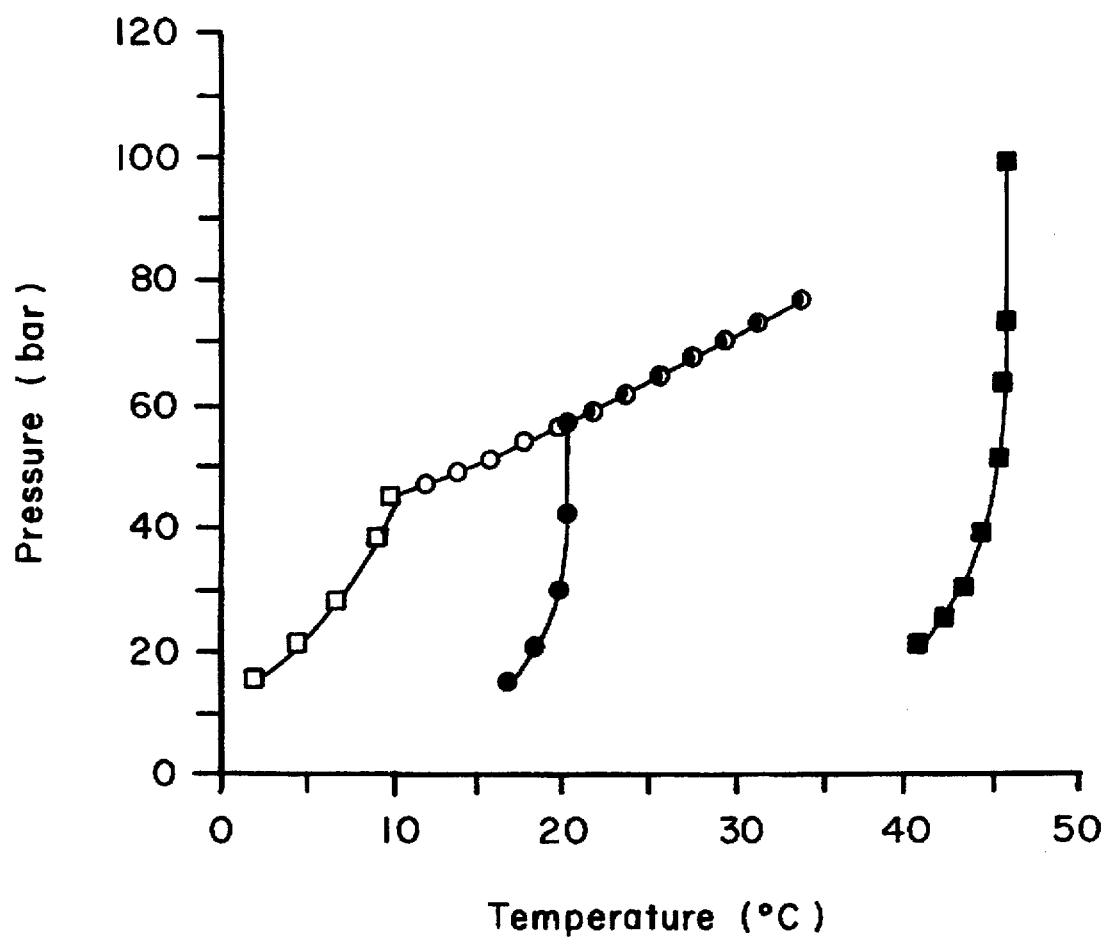
FIG. 2 is a pressure-temperature diagram obtained at the equilibrium conditions; and, FIG. 3 is a temperature-composition diagram obtained at the 30 bar isobaric condition.

Three-phase, i.e., vapour-liquid phenol-clathrate, equilibria for the binary phenol-carbon dioxide system were determined: the dissociation pressures at the temperature of 41.0°, 42.4°, 43.5°, 44.6°, 45.6°, 45.9°, 46.0° and 46.1° C. were 21.0, 25.1, 30.3, 39.5, 51.6, 63.1, 73.1 and 99.2 bar, respectively, which were depicted as ( - - ■ - - ) in FIG. 2.

Four-phase, i.e., vapour-liquid water-liquid phenol-clathrate, equilibria for the ternary phenol-water-carbon dioxide system were determined: the dissociation pressures at the temperature of 16.9°, 18.7°, 20.0°, 20.4° and 20.5° C. were 15.0, 20.8, 30.0, 42.5 and 57.2 bar, respectively, which were depicted as ( - - ● - - ).in FIG. 2, wherein the result of 57.2 bar at 20.5° C. is a quintuple point at which five phases of vapour-liquid water-liquid phenol-liquid carbon dioxide-clathrate coexist.

Four-phase, i.e., vapour-liquid water-liquid carbon dioxide-clathrate, equilibria for the ternary phenol-water-carbon dioxide system were determined: the equilibrium pressures at the temperature of 12.1°, 14.0°, 15.9°, 17.9° and 20.0° C. were 47.2, 49.3, 51.5, 54.0 and 56.5 bar, respectively, which were depicted as ( - - ○ - - ) in FIG. 2.

Finally, four-phase, i.e., vapour-liquid water-liquid phenol-liquid carbon dioxide, equilibria for the ternary phenol-water-carbon dioxide system were determined: the equilibrium pressures at the temperature of 21.9°, 23.8°, 25.8°, 27.7°, 29.6°, 31.4°, 33.8° and 34.1° C. were 59.0, 61.7, 64.4, 67.2, 70.0, 72.7, 76.6 and 77.2 bar, respectively, which were depicted as --◐-- in FIG. 2, wherein the result of 77.2 bar at 34.1° C. represents a critical end point at which the liquid phase and vapour phase of carbon dioxide join with each other.

From the results above, it can be concluded that: a solid phenol clathrate exists in a stable state under the temperature of from 0° to 43° C. and the pressure of from 15 to 100 bar; and, in order to separate and purify phenol in an aqueous phenol solution, it is preferable to conduct the separation under the temperature of from 0° to 20° C. and the pressure condition of from 15 to 45 bar.

EXAMPLE 2

Concentration of phenol which exists in the respective phase was measured with the aid of gas chromatograph installed at the phase equilibrium apparatus employed in Example 1, while elevating temperature under an isobaric condition of 30 bar. At this time, temperature at the phase equilibrium point at which vapour phase-water liquid phase-hydrate-clathrate coexist was maintained at 6.2° C., temperature at the phase equilibrium point at which vapour phase-water liquid phase-clathrate coexist was maintained at 6.5, 8.8, 10.8, 12.4, 14.7 and 16.6° C., and temperature at the phase equilibrium at which vapour phase-water liquid phase-phenol liquid phase coexist was maintained at 30.02° and 40.0° C., respectively. The phenol concentrations measured at the above temperatures were depicted as ( - - ● - - ) in FIG. 3.

Figure 3:
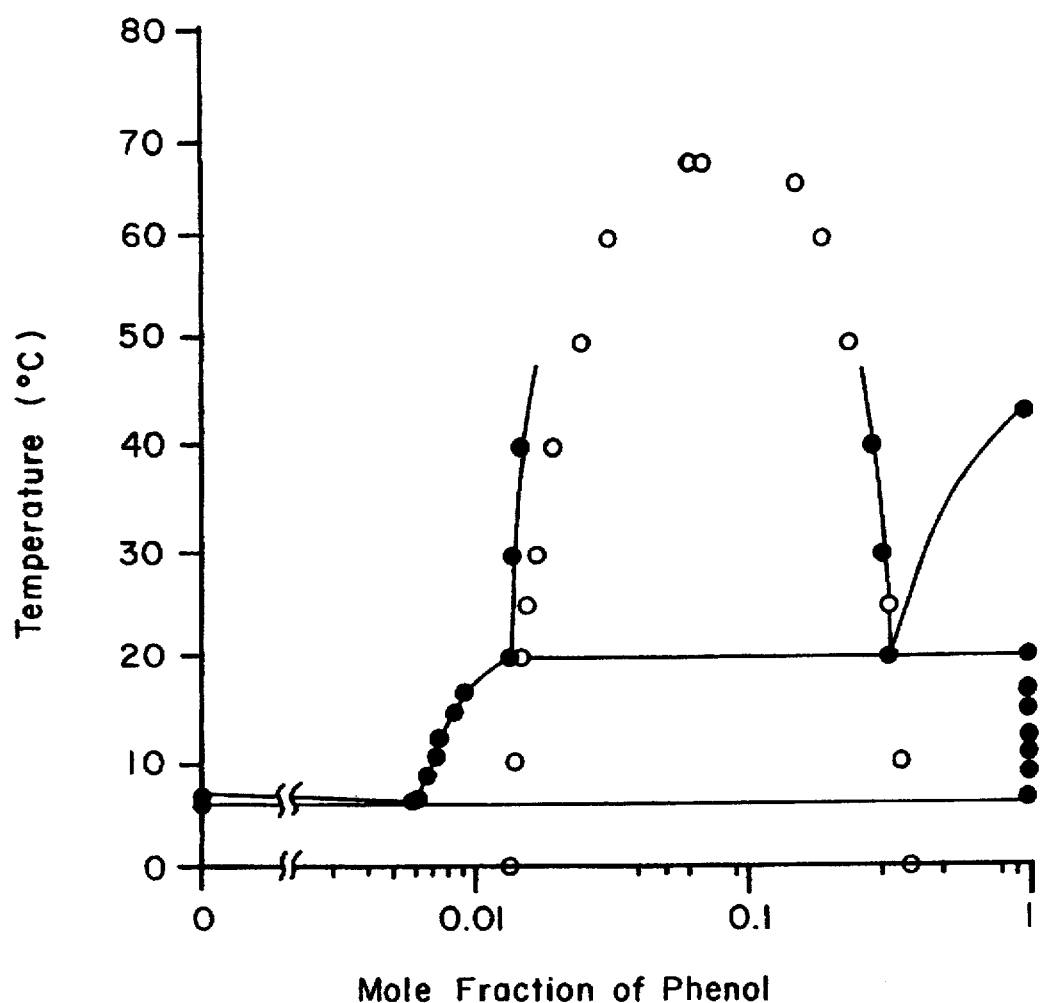

FIG. 3 represents a phase equilibrium diagram for a composition of water and phenol from which carbon dioxide is removed from the respective phases, where a phase equilibrium diagram for water-phenol two phases which exist under atmospheric pressure was also depicted as ( - - ○ - - ). As shown in FIG. 3, it is clearly determined that: when the content of phenol in an aqueous phenol solution ranges from 0.6 to 100 mole %, 100 mole % of a solid phenol and 0.6 mole % of an aqueous phenol solution can be obtained at the temperature of 6° to 20.0° C. under a pressure of 30 bar.

As clearly illustrated and demonstrated above, according to the method of separating phenol of the present invention, phenol can be separated from the highly concentrated phenol solution without employing solvent or post-treatment step, finally to give 100 mole % of a solid phenol and 0.6 mole % of an aqueous phenol solution by employing only one step. Moreover, since the method is carried out at the temperature of below room temperature without excess energy consumption, the separation of phenol can be made in a simple and economical manner.

What is claimed is:

1. A method of separating phenol from a highly concentrated phenol solution which comprises the step of forming a solid clathrate of phenol by adding high pressure carbon dioxide to the phenol solution.

2. The method of separating phenol from a highly concentrated phenol solution of claim 1 wherein the solid clathrate of phenol is formed at the temperature of 0° to 43° C.

3. The method of separating phenol from a highly concentrated phenol solution of claim 1 wherein the pressure of carbon dioxide is controlled in the range of 15 to 100 bars.

4. The method of separating phenol from a highly concentrated phenol solution of claim 1 wherein the phenol content of the phenol solution ranges from 30 mole % to 100 mole %.

5. The method of claim 4 wherein the pressure of carbon dioxide is controlled in the range of 15 to 45 bars and wherein the solid clathrate of phenol is formed at the temperature of 0° to 20° C.

* * * * *